United States Patent
Bartell

(10) Patent No.: US 7,130,458 B2
(45) Date of Patent: Oct. 31, 2006

(54) COMPUTER SOFTWARE SYSTEM, METHOD, AND PRODUCT FOR SCANNED IMAGE ALIGNMENT

(75) Inventor: Daniel M. Bartell, San Carlos, CA (US)

(73) Assignee: Affymetrix, Inc., Santa Clara, CA (US)

(*) Notice: Subject to any disclaimer, the term of this patent is extended or adjusted under 35 U.S.C. 154(b) by 674 days.

(21) Appl. No.: 10/197,369

(22) Filed: Jul. 17, 2002

(65) Prior Publication Data

US 2003/0038812 A1 Feb. 27, 2003

Related U.S. Application Data

(63) Continuation-in-part of application No. 09/681,819, filed on Jun. 11, 2001, now Pat. No. 6,829,376.

(60) Provisional application No. 60/306,119, filed on Jul. 17, 2001, provisional application No. 60/242,973, filed on Oct. 24, 2000.

(51) Int. Cl.
   *G06K 9/00* (2006.01)
   *G06K 9/32* (2006.01)
(52) U.S. Cl. ...................... 382/128; 382/294
(58) Field of Classification Search ......... 382/128–134
   See application file for complete search history.

(56) References Cited

U.S. PATENT DOCUMENTS

| | | | |
|---|---|---|---|
| 6,090,555 A | | 7/2000 | Fiekowsky et al. |
| 6,248,877 B1* | | 6/2001 | Bonner et al. ............. 536/25.3 |
| 6,349,144 B1 | | 2/2002 | Shams |
| 6,396,941 B1* | | 5/2002 | Bacus et al. ................ 382/128 |
| 6,571,005 B1* | | 5/2003 | Li et al. ..................... 382/133 |
| 6,674,885 B1* | | 1/2004 | Hansen et al. ............. 382/133 |
| 6,839,454 B1* | | 1/2005 | Park .......................... 382/128 |
| 2002/0025082 A1 | | 2/2002 | Kaushikkar |
| 2002/0047853 A1 | | 4/2002 | Bartell |
| 2002/0193962 A1 | | 12/2002 | Yakhini et al. |

OTHER PUBLICATIONS

Press Release dated Mar. 8, 2000, by Axon Instruments, Inc. entitled, "Axon Instruments Announces Release of GenePix Pro. 3.0"; http://www.axon.com/press/pr20000308.htm.
GenePix Pro Features; Axon Instruments, Inc. Foster City, CA, pp. 1-19.

* cited by examiner

*Primary Examiner*—Joseph Mancuso
*Assistant Examiner*—Hadi Akhavannik
(74) *Attorney, Agent, or Firm*—William R. McCarthy, III; Philip L. McGarrgle; Alan B. Sherr

(57) ABSTRACT

A computer program analyzes an image including features that correspond to emissions detected from a biological probe array. The program aligns one or more grids, each having one or more grid cells, with all or portions of the image; selects one or more grid cells to be associated with features based on distributions of pixel intensity values within the grid cells; locates a shape, such as a circle, in each selected grid cell based on distributions of pixel intensity values within the grid cells; and associates one or more intensity values with a feature based on intensities of feature pixels, or feature pixels and portions of feature pixels, within the shape located in the selected grid cell associated with the feature. The features may correspond to spots of biological material such as nucleic acid, peptide, protein fragment, protein, antibody, ligand, receptor, or small molecule.

32 Claims, 10 Drawing Sheets

ALONG Y   DISTANCE (PIXEL)

ALONG X   DISTANCE (PIXEL)

COMPUTER SOFTWARE SYSTEM, METHOD, AND PRODUCT FOR SCANNED IMAGE ALIGNMENT

RELATED APPLICATION

The present application claims priority from U.S. Provisional Patent Application Ser. No. 60/306,119, titled "Computer Software System, Method, and Product for Scanned Image Alignment Employing Improved Image Analysis Techniques," filed Jul. 17, 2001, which is hereby incorporated herein by reference in its entirety for all purposes. The present application also is a continuation in part of U.S. patent application Ser. No. 09/681,819, titled "Computer Software System, Method, and Product for Scanned Image Alignment," filed Jun. 11, 2001 now U.S. Pat. No. 6,829,376, which claims priority from U.S. Provisional Patent Application No. 60/242,973, titled "System, Method, and Product for Scanned Image Alignment," filed Oct. 24, 2000, both of which also are hereby incorporated herein by reference in their entireties for all purposes.

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

BACKGROUND OF THE INVENTION

1. Field of the Invention

The present invention relates to computer systems, methods, and products for analyzing images and, more particularly, for aligning grids on scanned images of high-density arrays of biological materials and analyzing pixilated information within individual grid elements.

2. Related Art

Spotted arrays, such as those made using the Affymetrix® 417™ or 427™ Arrayer from Affymetrix, Inc. of Santa Clara, Calif., are widely used to generate information about biological systems. Also, synthesized probe arrays, such as Affymetrix® GeneChip® arrays, have been used to generate unprecedented amounts of information about biological systems. For example, the GeneChip® Human Genome U133 Set (HG-U133A and HG-U133B) is made up of two microarrays containing over 1,000,000 unique oligonucleotide features covering more than 39,000 transcript variants that represent more than 33,000 human genes. Experimenters can quickly design follow-on experiments with respect to genes, EST's, or other biological materials of interest by, for example, producing in their own laboratories microscope slides containing dense arrays of probes using the Affymetrix® 417™ or 427™ Arrayer, or other spotting device.

Analysis of data from experiments with synthesized and/or spotted probe arrays may lead to the development of new drugs and new diagnostic tools. In some applications, this analysis begins with the capture of fluorescent signals indicating hybridization of labeled target samples with probes on synthesized or spotted probe arrays. The devices used to capture these signals often are referred to as scanners, an example of which is the Affymetrix® 428™ Scanner.

There is a great demand in the art for methods for organizing, accessing and analyzing the vast amount of information collected by scanning microarrays. Computer-based systems and methods have been developed to assist a user to obtain, analyze, and visualize the vast amounts of information generated by the scanners. These commercial and academic software applications typically provide such information as intensities of hybridization reactions or comparisons of hybridization reactions. This information may be displayed to a user in graphical form. In particular, data representing detected emissions conventionally are stored in a memory device of a computer for processing. The processed images may be presented to a user on a video monitor or other device, and/or operated upon by various data processing products or systems. Techniques are known for identifying the data representing detected emissions and separating them from background information. For example, U.S. Pat. No. 6,090,555 to Fiekowsky, et al., which is hereby incorporated by reference herein in its entirety for all purposes, describes various of these techniques.

SUMMARY OF THE INVENTION

In accordance with some embodiments of the present invention, methods are described for analyzing biological activity from a pixilated scanned image of a probe array, wherein the image includes a plurality of features corresponding to emissions detected from the probe array. The method includes the acts of (a) aligning a first grid having one or more first-grid cells with a first portion of the image; (b) selecting one or more of the first-grid cells to be associated with features based, at least in part, on distributions of pixel intensity values within the first-grid cells; (c) selecting from pixels within each selected first-grid cell a subset of first feature pixels, or pixels and portions of pixels, based, at least in part, on distributions of pixel intensity values within the selected first-grid cell; and (d) associating one or more intensity values with a feature based, at least in part, on intensities of the first feature pixels, or pixels and portions of pixels, of a selected first-grid cell. The probe array may be a spotted probe array and the features correspond to spots of biological material including any one or more of nucleic acid, peptide, protein fragment, protein, antibody, ligand, receptor, or small molecule. The method may also include (e) aligning a second grid having one or more second-grid cells with a second portion of the image; (f) selecting one or more of the second-grid cells to be associated with features based, at least in part, on distributions of pixel intensity values within the second-grid cells; (g) selecting from pixels within each selected second-grid cell a subset of second feature pixels, or pixels and portions of pixels, based, at least in part, on distributions of pixel intensity values within the selected second-grid cell; and (h) associating one or more intensity values with a feature based, at least in part, on intensities of the second feature pixels, or pixels and portions of pixels, of a selected second-grid cell.

In accordance with another embodiment, a method is described for analyzing a pixilated image having a plurality of features corresponding to emissions detected from a probe array. The method includes the acts of (a) aligning a first grid having one or more first-grid cells with a first portion of the image; (b) selecting one or more of the first-grid cells to be associated with features based, at least in part, on distributions of pixel intensity values within the first-grid cells; (c) locating a first shape in each selected first-grid cell based, at least in part, on distributions of pixel intensity values within the first-grid cells; and (d) associating one or more intensity values with a feature based, at least in part, on intensities of feature pixels, or feature pixels and portions of feature pixels, within the shape located in the selected first-grid cell associated with the feature. As will be appreciated by those of ordinary skill in the relevant art, shapes (as well as grid lines, features, and so on) may be presented in the form of pixels on an output device for viewing by a user, and terms such as "locating" and "shape" are used in recognition of this context. However, the terms are not limited to literal viewing or display of pixels, but include representations of pixels and their relationships in the form of data stored in a computer memory or other memory or storage device. That is, in some implementations, the functions described may be carried out by manipulation of data rather than (or in addition to) presentation of corresponding graphical elements to a user. In these and other embodiments, the probe array may be a spotted probe array and the features may correspond to spots of biological material such as nucleic acid, peptide, protein fragment, protein, antibody, ligand, receptor, and/or small molecule.

In accordance with other embodiments, a computer program product is described for analyzing a pixilated image of a probe array, wherein the image includes a plurality of features corresponding to emissions detected from the probe array. The product includes a grid aligner constructed and arranged to align one or more grids, each having one or more grid cells, with all or portions of the image; a feature associator constructed and arranged to select one or more grid cells to be associated with features based, at least in part, on distributions of pixel intensity values within the grid cells; and a feature locator constructed and arranged to select from pixels within each selected grid cell a subset of feature pixels, or feature pixels and portions of feature pixels, based, at least in part, on distributions of pixel intensity values within the selected grid cell. The product may also include an intensity determiner constructed and arranged to associate one or more intensity values with a feature based, at least in part, on intensities of the feature pixels, or pixels and portions of pixels, of a selected grid cell.

In a further embodiment, a further computer program product is described for analyzing a pixilated image having a plurality of features corresponding to emissions detected from a probe array. It includes a grid aligner constructed and arranged to align one or more grids, each having one or more grid cells, with all or portions of the image; a feature associator constructed and arranged to select one or more grid cells to be associated with features based, at least in part, on distributions of pixel intensity values within the grid cells; a feature locator constructed and arranged to locate a shape in each selected grid cell based, at least in part, on distributions of pixel intensity values within the grid cells; and, optionally, an intensity determiner constructed and arranged to associate one or more intensity values with a feature based, at least in part, on intensities of feature pixels, or feature pixels and portions of feature pixels, within the shape located in the selected grid cell associated with the feature.

A scanning system is described in accordance with yet another embodiment. It includes a scanner constructed and arranged to scan a probe array to generate a pixilated image having a plurality of features corresponding to emissions detected from the probe array and a computer having a processor and memory unit. Also included in the system is a computer program product constructed and arranged for storage in the memory unit and execution by the processor. The program includes a grid aligner constructed and arranged to align one or more grids, each having one or more grid cells, with all or portions of the image, a feature associator constructed and arranged to select one or more grid cells to be associated with features based, at least in part, on distributions of pixel intensity values within the grid cells, a feature locator constructed and arranged to locate a shape in each selected grid cell based, at least in part, on distributions of pixel intensity values within the grid cells, and an intensity determiner constructed and arranged to associate one or more intensity values with a feature based, at least in part, on intensities of feature pixels, or feature pixels and portions of feature pixels, within the shape located in the selected grid cell associated with the feature.

The above embodiments, implementations, and aspects are not necessarily inclusive or exclusive of each other and may be combined in any manner that is non-conflicting and otherwise possible, whether they be presented in association with a same, or a different, aspect of the invention. The description of one embodiment, implementation, or aspect is not intended to be limiting with respect to other embodiments or implementations. Also, any one or more function, step, operation, or technique described elsewhere in this specification may, in alternative embodiments or implementations, be combined with any one or more function, step, operation, or technique described in the summary. Thus, the above embodiments, implementations, and aspects are illustrative rather than limiting.

BRIEF DESCRIPTION OF THE DRAWINGS

The above and further features will be more clearly appreciated from the following detailed description when taken in conjunction with the accompanying drawings. In the drawings, like reference numerals indicate like structures or method steps and the leftmost digit of a reference numeral indicates the number of the figure in which the referenced element first appears (for example, the element 125 appears first in FIG. 1). In functional block diagrams, rectangles generally indicate functional elements, parallelograms generally indicate data, and rectangles with a pair of double borders generally indicate predefined functional elements. In method flow charts, rectangles generally indicate method steps and diamond shapes generally indicate decision elements. All of these conventions, however, are intended to be typical or illustrative, rather than limiting.

DETAILED DESCRIPTION

Figure 1:
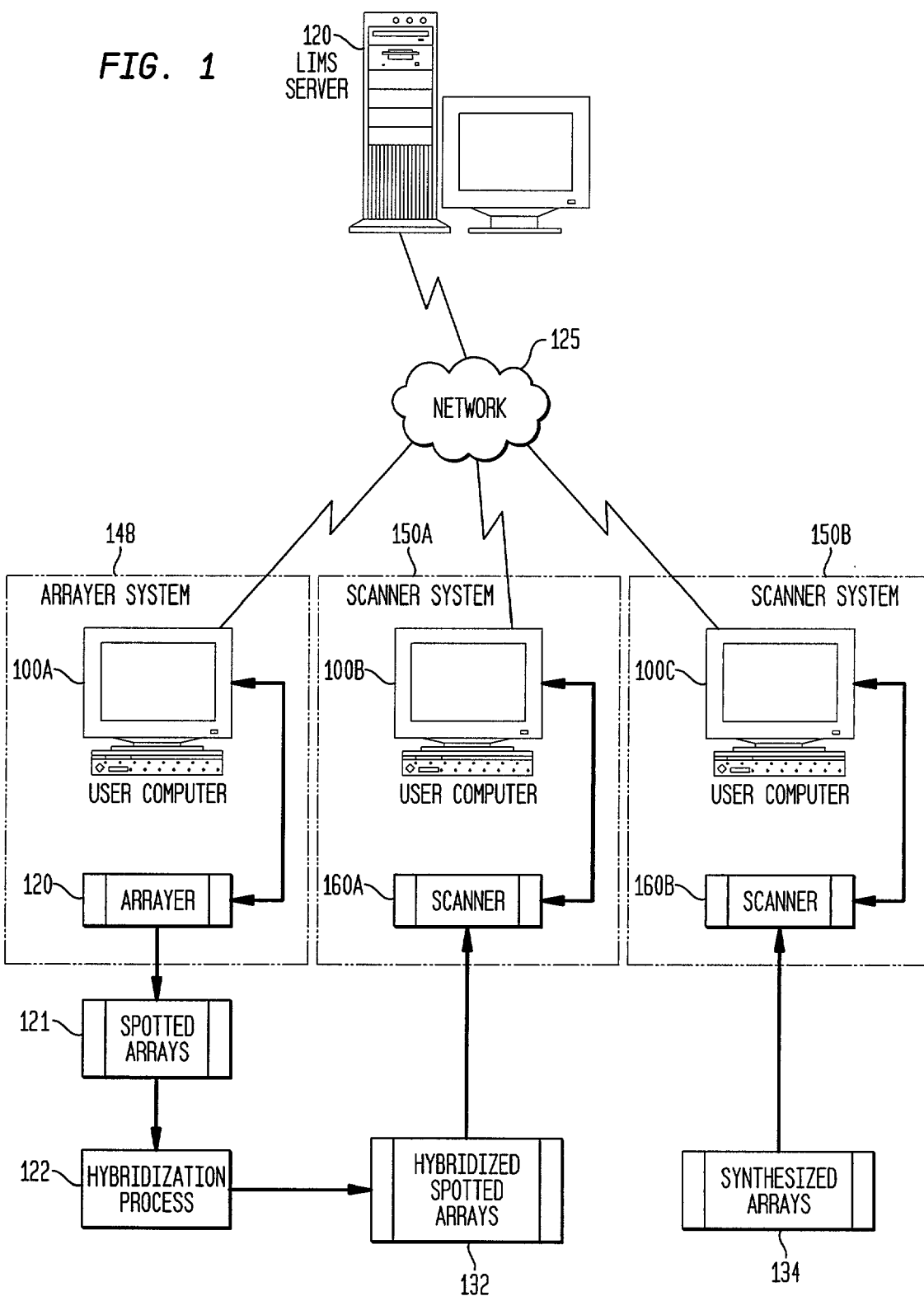
FIG. 1 is a simplified schematic diagram of an illustrative implementation of networked systems for generating, sharing, and processing probe array data among computers on a network, including an arrayer system for generating spotted probe arrays and scanner systems for scanning spotted and synthesized probe arrays.

Systems, methods, and software products to acquire, process, analyze, and/or display data from experiments with synthesized and/or spotted arrays are described herein with respect to illustrative, non-limiting, implementations. Various other alternatives, modifications and equivalents are possible. For example, while illustrative implementations of systems, methods, and computer software products may be described with reference to spotted arrays made with Affymetrix™ Arrayers or analyzed using Affymetrix™ scanners and/or software, the systems, methods, and products of the present invention are not so limited. For example, they generally may be applied with respect to many other types of probe arrays and, more generally, with respect to numerous parallel biological assays produced in accordance with other conventional technologies and/or produced in accordance with techniques that may be developed in the future.

Probe Arrays: For example, aspects of the systems, methods, and products described herein may, in some implementations, be applied to parallel assays of nucleic acids, PCR products generated from cDNA clones, proteins, antibodies, or many other biological materials. These materials may be disposed on microscope slides, on substrates employed for GeneChip® arrays, or on beads, optical fibers, or other substrates, supports, or media (all or any of which may hereafter generally and collectively be referred to as "substrates"). Moreover, with respect to some implementations in which the context so indicates or allows, the probes need not be immobilized in or on a substrate, and, if immobilized, need not be disposed in regular patterns or arrays. For convenience, the term "probe array" will generally be used broadly hereafter to refer to all of these types of arrays and parallel biological assays.

For convenience, an array made by depositing or positioning pre-synthesized or pre-selected probes on a substrate, or by depositing/positioning techniques that may be developed in the future, is hereafter referred to as a "spotted array." Typically, spotted arrays (such as represented schematically by spotted arrays 121 of FIG. 1) are fabricated on microscope slides, although other substrates may be used as noted, for example, in U.S. Pat. Nos. 6,329,143, 6,310,189, 6,309,831, 6,197,506, and 5,744,305, all of which are hereby incorporated by reference herein in their entireties for all purposes. These arrays typically consist of liquid spots containing biological material of potentially varying compositions and concentrations. For instance, a spot in the array may include a few strands of short oligonucleotides in a water solution, or it may include a high concentration of long strands of complex proteins. Thus, numerous types of materials may be analyzed using the systems, methods, and products described herein. As additional non-limiting examples, the spots (also referred to as "probes" of the resulting probe array) may include cells, proteins, nucleic acid sequences representing genes or EST's, or other biological elements. More specifically, the probes may be a ligand, receptor, peptide, nucleic acid (oligonucleotide or polynucleotide of RNA or DNA), protein fragment, small molecule, or any other of the biological molecules listed in U.S. Pat. No. 5,445,934 (hereby incorporated by reference herein in its entirety for all purposes) at column 5, line 66 to column 7, line 51. Thus, as a non-limiting example, a probe may refer to a nucleic acid, such as an oligonucleotide, capable of binding to a nucleic acid of complementary sequence through one or more types of chemical bonds, usually through complementary base pairing, usually through hydrogen bond formation. A probe may include natural (i.e. A, G, U, C, or T) or modified bases (7-deazaguanosine, inosine, etc.). In addition, the bases in probes may be joined by a linkage other than a phosphodiester bond, so long as the bond does not interfere with hybridization. Thus, probes may be peptide nucleic acids in which the constituent bases are joined by peptide bonds rather than phosphodiester linkages. Other examples of probes include antibodies used to detect peptides or other molecules, or any ligands for detecting its binding partners. When referring to probes (or targets, described below) as nucleic acids, it should be understood that these are illustrative examples that are not to limit the invention in any way.

The Affymetrix® 417™, 427™ and 437™ Arrayers are devices that deposit densely packed arrays of biological material on a microscope slide in accordance with aspects of these techniques. Aspects of these, and other, spot arrayers are described in U.S. Pat. Nos. 6,040,193 and 6,136,269; in PCT Applications Nos. PCT/US99/00730 (International Publication Number WO 99/36760), PCT/US01/04285, and PCT/US02/13383; and in U.S. patent application Ser. Nos. 09/501,099, 09/122,216, 09/683,298, and 09/862,177, all of which are hereby incorporated by reference in their entireties for all purposes. Other techniques for depositing or positioning biological probes on a substrate also exist. For example, U.S. Pat. No. 6,040,193 to Winkler, et al. is directed to processes for dispensing drops of biological material. The '193 patent, and U.S. Pat. No. 5,885,837 to Winkler, also describe separating reactive regions of a substrate from each other by inert regions and spotting on the reactive regions. The '193 and '837 patents are hereby incorporated by reference in their entireties. Other techniques are based on ejecting jets of biological material. Other implementations of the jetting technique may use devices such as syringes or piezo electric pumps to propel the biological material. Various aspects of producing probe arrays and related operations are also described in U.S. Pat. Nos. 6,329,143; 6,309,831; 6,271,957; 6,269,846; 6,261,776; 6,239,273; 6,238,862; 6,156,501; 6,150,147; 6,136,269; 6,121,048; 6,040,193; 5,885,837; 5,837,832; 5,831,070; 5,770,722; 5,744,305; 5,677,195; 5,599,695; 5,583,211; 5,554,501; 5,491,074; 5,482,867; 5,429,807; and 5,384,261, all of which are hereby incorporated herein in their entireties for all purposes.

Spotted arrays typically are used in conjunction with tagged biological samples such as cells, proteins, genes or EST's, other DNA sequences, or other biological elements. These samples, referred to herein as "targets," may be processed in some implementations based on their spatial association with certain probes in the probe array. For example, one or more chemically tagged biological samples, i.e., the targets, are distributed over the probe array in a typical implementation. Some targets hybridize with at least partially complementary probes and remain at the probe locations, while non-hybridized targets are washed away. These hybridized targets, with their "tags" or "labels," are thus spatially associated with the targets' complementary probes. The hybridized probe and target may sometimes be referred to as a "probe-target pair." Detection of these pairs can serve a variety of purposes, such as to determine whether a target nucleic acid has a nucleotide sequence identical to or different from a specific reference sequence. See, for example, U.S. Pat. No. 5,837,832 to Chee, et al. Other uses include gene expression monitoring and evaluation (see, e.g., U.S. Pat. No. 5,800,992 to Fodor, et al.; U.S. Pat. No. 6,040,138 to Lockhart, et al.; and International App. No. PCT/US98/15151, published as WO99/05323, to Balaban, et al.), genotyping (U.S. Pat. No. 5,856,092 to Dale, et al.), or other detection of nucleic acids. The '832, '992, '138, and '092 patents, and publication WO99/05323, are incorporated by reference herein in their entirety for all purposes.

To ensure proper interpretation of the term "probe" as used herein, it is noted that contradictory conventions exist in the relevant literature. The word "probe" is used in some contexts to refer not to the biological material that is deposited on a substrate, as described above, but to what has been referred to herein as the "target." To avoid confusion, the term "probe" is used herein to refer to probes such as those deposited to create spotted arrays.

FIG. 1 is a simplified schematic diagram of illustrative systems for generating, sharing, and processing data derived from experiments using probe arrays (e.g., spotted arrays and/or synthesized arrays). More particularly, an illustrative arrayer system 148 and illustrative scanner systems 150A and 150B (collectively, scanner systems 150) are shown. In this example, data may be communicated among user computer 101A of system 148, user computers 100B and 100C of systems 150, and Laboratory Information Management (LIMS) server 120 over network 125. LIMS server 120 and associated software generally provides data capturing, tracking, and analysis functions from a centralized infrastructure. Aspects of illustrative LIMS are described in U.S. patent application Ser. Nos. 09/683,912 and 09/682,098; and in U.S. Provisional Patent Applications Nos. 60/220,587 and 60/273,231, all of which are hereby incorporated by reference herein for all purposes. LIMS server 120 and network 125 are optional, and the systems in other implementations may include a scanner for spotted arrays and not synthesized arrays, or vice versa. Also, rather than employing separate user computers 101A, 100B, and 100C to operate and process data from an arrayer and scanner, respectively, as in the illustrated implementation, a single computer may be used for all of these purposes in other implementations. Further, any of these computers, or any functional components thereof, may also or in addition be integral to arrayer 120 or to scanner 160 in some implementations so that, for example, they are located within the same housing as the arrayer or scanners.

More generally, a large variety of computer and/or network architectures and designs may be employed, and it will be understood by those of ordinary skill in the relevant art that many components of typical computer network systems are not shown in FIG. 1 for sake of clarity.

Scanner 160: Any of a variety of conventional techniques, or ones to be developed in the future, may be used to generate probe-target pairs in probe arrays that may be detected using a scanner such as illustrative scanners 160A or 160B (generally and collectively referred to as scanner 160). As one illustrative example that will be familiar to those of ordinary skill in the relevant art, conventional fluidics stations, hybridization chambers, and/or various manual techniques (as, for example, generally and collectively represented by hybridization process 122 in FIG. 1) may be used to apply one or more labeled targets to spotted arrays on microscope slides. In a particular implementation, for instance, sample of a first target may be labeled with a first dye (an example of what may more generally be referred to hereafter as an "emission label") that fluoresces at a particular characteristic frequency, or narrow band of frequencies, in response to an excitation source of a particular frequency. A second target may be labeled with a second dye that fluoresces at a different characteristic frequency. The excitation source for the second dye may, but need not, have a different excitation frequency than the source that excites the first dye, e.g., the excitation sources could be the same, or different, lasers. The target samples may be mixed and applied to the probes of spotted arrays on microscope slides, and conditions may be created conducive to hybridization reactions, all in accordance with known techniques. In accordance with other techniques, such as typically are applied with respect to Affymetrix® GeneChip® synthesized arrays, samples of one labeled target are applied to one array and samples of a second labeled target are applied to a second array having the same probes as the first array. Hybridization techniques are applied to both arrays. For example, hybridized synthesized arrays 134 of FIG. 1 may be illustratively assumed to be two GeneChip® synthesized arrays that have been subject to hybridization processes with respect to two different target samples, each labeled with different fluorescent dyes. See, e.g., U.S. Pat. No. 6,114,122, which is hereby incorporated by reference herein in its entirety.

Many scanner designs may be used to provide excitation signals to excite labels on targets or probes, and to detect the emission signals from the excited labels. In references herein to illustrative implementations, the term "excitation beam" may be used to refer to light beams generated by lasers to provide the excitation signal. However, excitation sources other than lasers may be used in alternative implementations. Thus, the term "excitation beam" is used broadly herein. The term "emission beam" also is used broadly herein. As noted, a variety of conventional scanners detect fluorescent or other emissions from labeled target molecules or other material associated with biological probes. Other conventional scanners detect transmitted, reflected, or scattered radiation from such targets. In other implementations, radionucleotide or other types of emissions may be detected with or without the involvement of an excitation or enabling source. These processes are sometimes generally and collectively referred to hereafter for convenience simply as involving the detection of "emission beams." The signals detected from the emission beams are generally referred to hereafter as "emission signals" and this term is intended to have a broad meaning commensurate with that intended herein for the term "emission beams."

Various detection schemes are employed depending on the type of emissions and other factors. A typical scheme employs optical and other elements to provide an excitation beam, such as from a laser, and to selectively collect the emission beams. Also generally included are various light-detector systems employing photodiodes, charge-coupled devices, photomultiplier tubes, or similar devices to register the collected emission beams. Illustrative scanners or scanning systems that may, in various implementations, be included in scanner systems 150 are described in U.S. Pat. Nos. 5,143,854, 5,578,832, 5,631,734, 5,834,758, 5,936, 324, 5,981,956, 6,025,601, 6,141,096, 6,185,030, 6,201,639, 6,218,803, and 6,252,236; in PCT Application PCT/US99/

06097 (published as WO99/47964); in U.S. patent applications Ser. Nos. 10/063,284, 09/683,216, 09/683,217, 09/683,219, 09/681,819, and 09/383,986; and in U.S. Provisional Patent Applications Serial Nos. 60/364,731, and 60/286,578, each of which is hereby incorporated herein by reference in its entirety for all purposes.

The scanning system provides data representing the intensities (and possibly other characteristics, such as color) of the detected emissions, as well as the locations on the substrate where the emissions were detected. The data typically are stored in a memory device in the form of a data file. One type of data file, sometimes referred to as an "image file," typically includes intensity and location information corresponding to elemental sub-areas of the scanned substrate. The term "elemental" in this context means that the intensities, and/or other characteristics, of the emissions from this area each are represented by a single value. When displayed as an image for viewing or processing, elemental picture elements, or pixels, often represent this information. Thus, for example, a pixel may have a single value representing the intensity of the elemental sub-area of the substrate from which the emissions were scanned. The pixel may also have another value representing another characteristic, such as color. For instance, a scanned elemental sub-area in which high-intensity emissions were detected may be represented by a pixel having high luminance (hereafter, a "bright" pixel), and low-intensity emissions may be represented by a pixel of low luminance (a "dim" pixel). Alternatively, the chromatic value of a pixel may be made to represent the intensity, color, or other characteristic of the detected emissions. Thus, an area of high-intensity emission may be displayed as a red pixel and an area of low-intensity emission as a blue pixel. As another example, detected emissions of one wavelength at a particular sub-area of the substrate may be represented as a red pixel, and emissions of a second wavelength detected at another sub-area may be represented by an adjacent blue pixel. Many other display schemes are known.

Probes need not have been synthesized or deposited on all areas of the substrate. On an Affymetrix® GeneChip® array, for example, the "synthesized region" of the entire nucleic acid array typically is bordered by a non-synthesized area. Because the non-synthesized area does not contain probes, labeled targets do not hybridize there and the scanning system ideally should not detect emissions. However, various imperfections may give rise to the detection of background emissions from non-synthesized areas, or from synthesized areas in which hybridization has not occurred. The term "background noise" may be used hereafter to refer to these detected background emissions and noise from other sources.

Generally, a human being may inspect a printed or displayed image constructed from the data in an image file and may identify those features that are bright or dim, or are otherwise identified by a pixel characteristic (such as color). However, it frequently is desirable to provide this information in an automated, quantifiable, and repeatable way that is compatible with various image processing and/or analysis techniques. For example, the information may be provided to a computer that associates the locations where hybridized targets were detected (i.e., features were detected) with known locations where probes of known identities were synthesized or deposited. Information such as the nucleotide or monomer sequence of target DNA or RNA may then be deduced. Techniques for making these deductions are described, for example, in U.S. Pat. No. 5,733,729, which hereby is incorporated by reference in its entirety for all purposes, and in U.S. Pat. No. 5,837,832, noted and incorporated above. Among other purposes, the data may be used to study genetic characteristics and to detect mutations relevant to genetic and other diseases or conditions.

In order to facilitate computer processing of the pixel information, it therefore typically is desirable to automate the identification of pixels having particular characteristics and relate them to the known locations of probes. To this end, computer-implemented image processing techniques have been developed to "align" the scanned image file. That is, the techniques attempt to identify which pixels represent emissions from which probes, and to distinguish this information from background noise. Background noise could include, for example, dust, fingerprints, particles, scratches, or numerous other sources of fluorescent signal generally unrelated to hybridized probe-target pairs. Some of these techniques are described in U.S. Pat. No. 6,090,555 to Fiekowsky, et al., incorporated by reference above. Generally speaking, one aspect of the technique described in the '555 patent operates on a pattern, such as a checkerboard pattern, that is known to be included in the scanned image. When the image is convolved with a filter, a recognizable pattern, such as a grid pattern, is generated in the convolved image. The scanned image may then be aligned according to the position of the recognizable pattern in the convolved image. In some implementations of these techniques, a grid is aligned over the scanned image and the position of the grid is adjusted to minimize a sum of the intensities of pixels along a grid direction.

Applications of this and other techniques may be complicated, however, when extreme, aberrant, or unexpected conditions are encountered during the scanning process, or when features of alignment patterns have indistinct edges for any of a variety of reasons. Also, as in the reading of a scanned spotted array image for example, the contours of the hybridized feature, as represented by the image detected from fluorescent emissions, may be indistinct, irregular, mixed with scratches, background noise, spurious signal, or otherwise distorted. Further, the image representing the spot feature may not be located in a grid cell in a determinable position, such as at the cell's center. Translations of the feature to off-center locations within a grid cell may be due to non-linearity or other irregularities in the scanner (e.g., aberrations in scanning speed or pixel clock timing), irregular spacing among depositing elements (e.g., a depositing pin may be bent or a depositing element may be misaligned in a print head), or other factors. In order accurately to determine a feature's intensity or other characteristic representing a biological activity, such as degree of hybridization, the location and extent of a feature within a grid cell must be determined even if the feature is off-center or otherwise translated within the cell. Specific, non-limiting, implementations are now described that address these and other problems.

Figure 2:
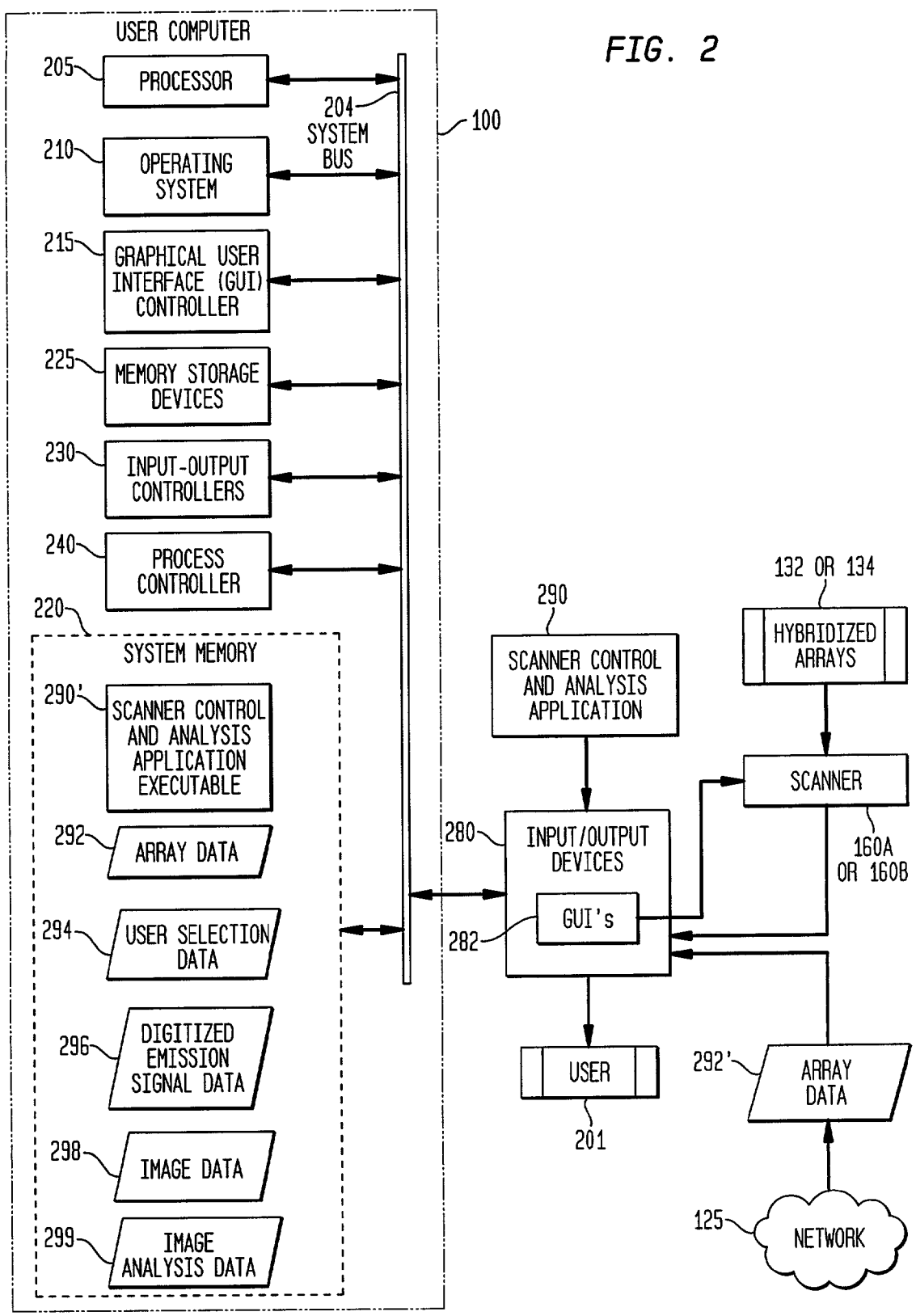
FIG. 2 is a functional block diagram of an illustrative implementation of a scanner system such as those of FIG. 1, including an illustrative computer and illustrative scanner.

User Computer 100B or 100C: As shown in FIG. 1 and noted above, scanner 160 operates in the illustrated implementation under computer control, e.g., under the control of user computers 100B or 100C (generally and collectively referred to as computer 100), as shown in greater detail in FIG. 2. Although computer 100 is shown in FIGS. 1 and 2 for clarity as being directly coupled to scanner 160, it may alternatively be coupled to scanner 160 over a local-area, wide-area, or other network, including an intranet and/or the Internet. Computer 100 may be a personal computer, a workstation, a server, or any other type of computing platform now available or that may be developed in the future. A typical configuration of computer 100 is shown in FIG. 2 including known components such as processor (e.g., CPU) 205, operating system 210, system memory 220, memory storage devices 225, GUI controller 215, and input-output controllers 230, all of which typically communicate in accordance with known techniques such as via system bus 204. It will be understood by those skilled in the relevant art that there are many possible configurations of the components of computer 100 and that some components that may typically be included in computer 100 are not shown, such as cache memory, a data backup unit, and many other devices.

Figure 4:
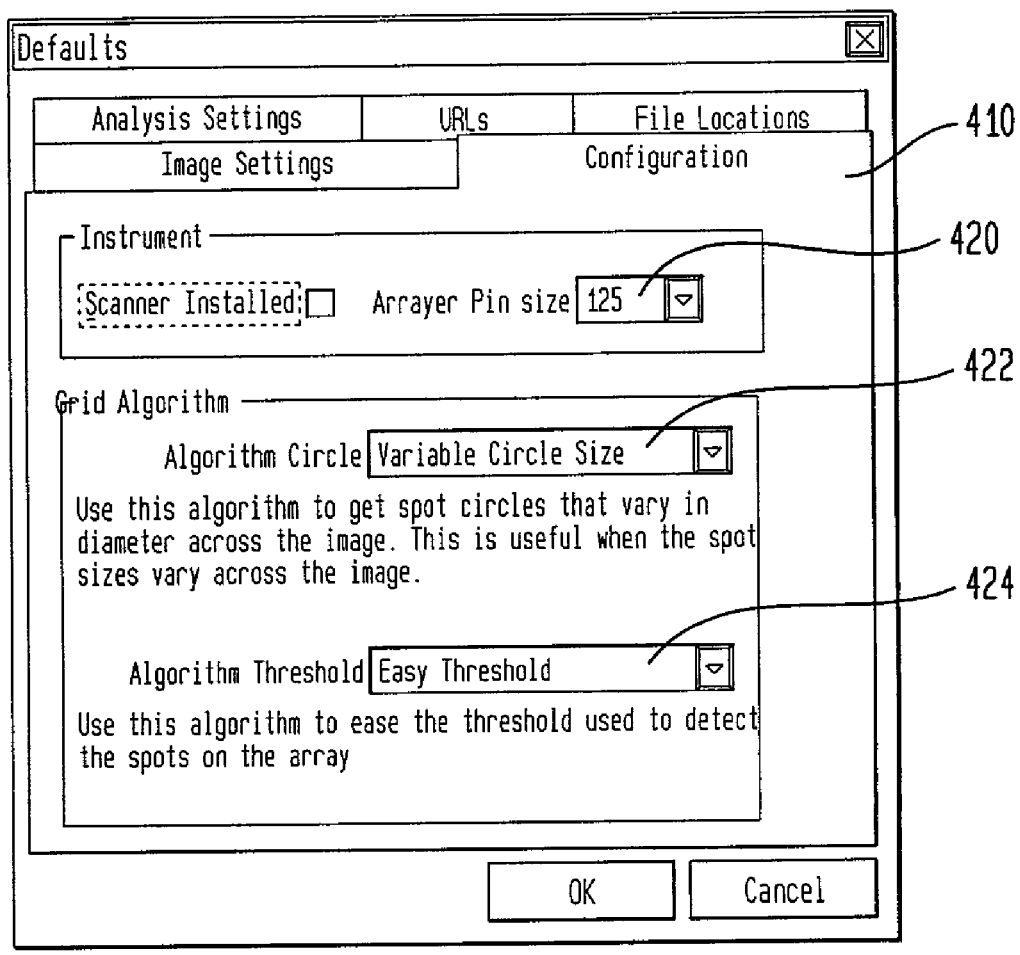
FIG. 4 is an illustrative implementation of a graphical user interface employed in cooperation with the application of FIG. 3 to receive user-specified grid parameter data.

Input-output controllers 230 could include any of a variety of known devices for accepting and processing information from a user, whether a human or a machine, whether local or remote. Such devices include, for example, modem cards, network interface cards, sound cards, or other types of controllers for any of a variety of known input devices. Output controllers of input-output controllers 230 could include controllers for any of a variety of known display devices for presenting information to a user, whether a human or a machine, whether local or remote. If one of these display devices provides visual information, this information typically may be logically and/or physically organized as an array of picture elements, sometimes referred to as pixels. Graphical user interface (GUI) controller 215 may comprise any of a variety of known or future software programs for providing graphical input and output interfaces between computer 100 and a user 201 (e.g., an experimenter wishing to use scanner 160 to acquire and analyze information from probe arrays), and for processing inputs from user 201 (hereafter sometimes referred to as user inputs or user selections). To avoid confusion, references hereafter to a "GUI" generally are directed to one or more graphical user interfaces displayed on a display device of devices 280 to user 201, such as GUI 282A of FIG. 4, described below. To be distinguished are references to a "GUI controller," such as GUI controller 215, that operates to display the GUI's to user 201 and to process input information provided by user 201 through the GUI's. As is well known in the relevant art, a user may provide input information using a GUI by selecting, pointing, typing, speaking, and/or otherwise operating, or providing information into, one or more input devices of devices 280 in a known manner.

Computer 100 may optionally include process controller 240 that may, for example, be any of a variety of PC-based digital signal processing (DSP) controller boards, such as the M44 DSP Board made by Innovative Integration of Simi Valley, Calif. More generally, controller 240 may be implemented in software, hardware or firmware, or any combination thereof.

Scanner Control and Analysis Application 290: Application 290 of the illustrated implementation is a software application that controls functions of scanner 160 and provides various image analysis functions. More specifically, when executed in coordination with processor 205, operating system 210, GUI controller 215, and/or process controller 240, illustrative application 290 performs user interface functions, data and image processing operations, and data transfer and storage operations related to data provided by or to scanner 160 and/or user 201, as described in greater detail below. Affymetrix® Jaguar™ 2.0 software, available from Affymetrix, Inc., is a commercial product that includes various aspects of the illustrated or other implementations of application 290, although the present invention is not limited to features or techniques present in that product.

As will be evident to those skilled in the relevant art, application 290 may be loaded into system memory 220 and/or memory storage device 225 through an input device of devices 280. Alternatively, application 290 may be implemented as executable instructions stored in firmware, or a combination of firmware and software (either in computer 100 as shown in this illustrative example, or in scanner 160 or elsewhere in other implementations). Executable code corresponding to application 290 is referred to as scanner control application executable 290' and is shown for convenience with respect to the illustrated implementation as stored in system memory 220. However, instructions and data including executable instructions of executable 290', and data used or generated by it, may be located in or shifted among other memory devices, local or remote, as convenient for data storage, data retrieval, and/or execution. The instructions of executable 290', also called computer control logic, when executed by processor 205, enable computer 100 to perform functions of the illustrated systems. Accordingly, executable 290' may be referred to as a controller of computer 100. More specifically, in some implementations, the present invention includes a computer program product comprising a computer usable medium having control logic (e.g., computer software program, including program code) stored therein. In various embodiments, software products may be implemented using any of a variety of programming languages, such as Visual C++ or Visual Basic from Microsoft Corporation, Java™ from Sun Microsystems, Inc., and/or other high or lower level programming languages. The control logic, when executed by processor 205, causes processor 205 to perform some of the functions of the invention, as described herein. In other embodiments, some functions of the present invention may be implemented primarily in hardware using, for example, a hardware state machine. Implementation of the hardware state machine so as to perform the functions described herein will be apparent to those skilled in the relevant arts.

Figure 3:
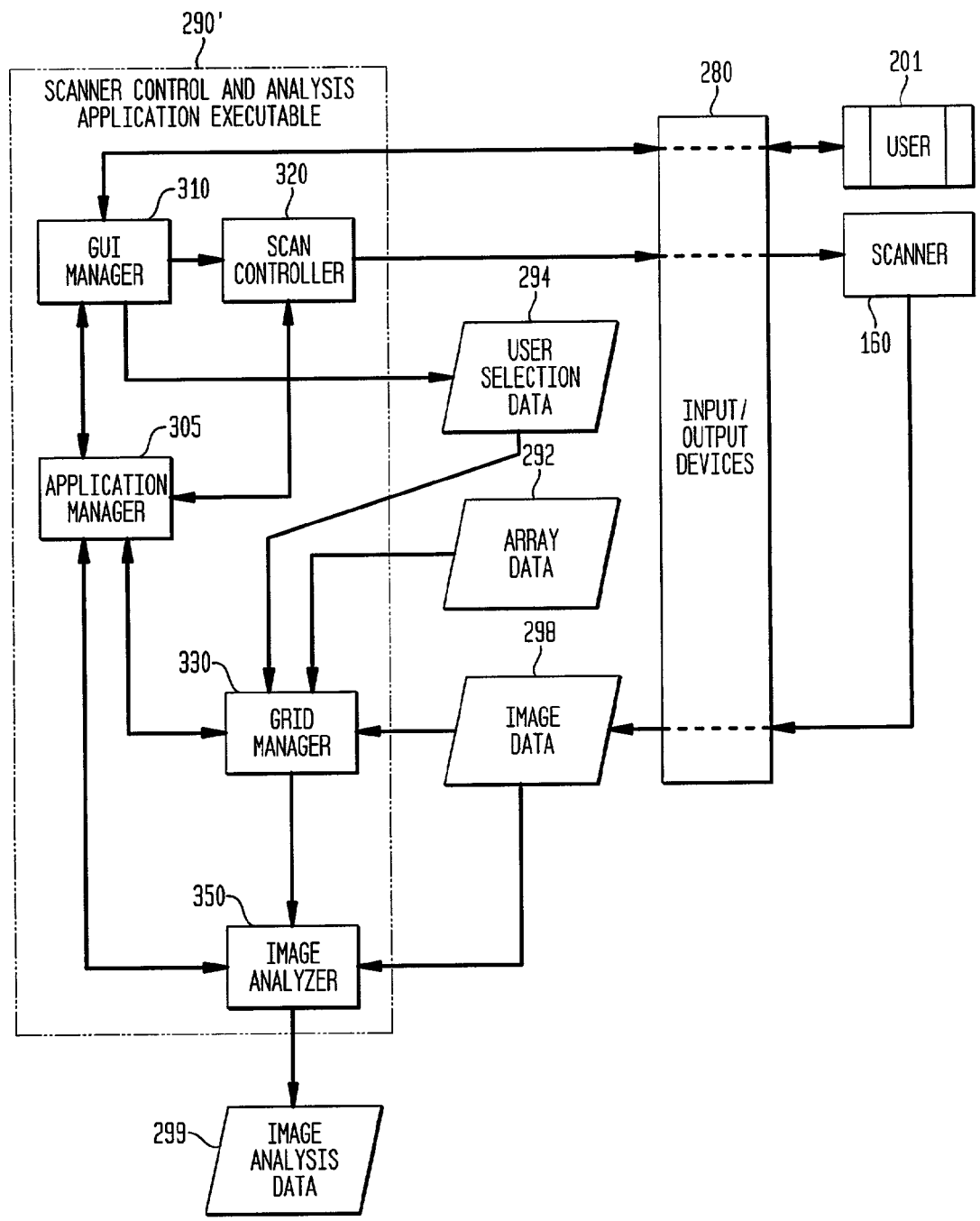
FIG. 3 is functional block diagram of one implementation of a scanner control and analysis application (i.e., computer program product), including a grid aligner, such as may be executed by the computer of FIG. 2 to control the scanner of FIG. 2 and analyze images generated, for example, from emission signals it provides.

As more particularly shown in FIG. 3, application 290 in the illustrated implementation includes an application manager 305 that, in accordance with known techniques, coordinates the functions of, and facilitates transfer of data among, other elements of application 290. Among those other elements in this implementation are GUI manager 310 that receives user selections for various parameters involved both in the functions of controlling scanner 160 and of analyzing image data 298 generated by scanner 160.

With respect to scan-control functions, scan controller 320 accepts from GUI manager 310 user selections relevant to scanner control and performs various functions involved in controlling the scanner such as focusing, scan-area adjustment, scan-speed adjustment, pixel-clock and pixel-data adjustments, and so on. Aspects of scan control are described with respect to illustrative implementations in U.S. Provisional Application, Ser. Nos. 09/682,071, 09/682,074, 09/682,076, which are hereby incorporated by reference herein in their entireties for all purposes, and in other patents or patent applications referred to and incorporated above. As described in greater detail in these and other patents or patent applications incorporated herein, scanner 160 generates data representing information from the hybridized microarray. As a non-limiting example, the data may represent intensities of fluorescent emissions from labels associated with hybridized probe-target pairs at known locations on the microarray. An example of such data is represented in FIG. 2 by digitized emission signal data 296 that is generated in response to an excitation beam directed by scanner 160 onto a hybridized array. Signal data 296 may in some implementations be transferred to system memory 220 where application executable 290' processes it to generate image data 298 that also is shown as stored in memory 220. For example, the Affymetrix® Jaguar 2.0 software application generates a data file in this manner that is given a "*.tif" extension to indicate that it is image data in a particular file format known to those of ordinary skill in the art. There are numerous conventional techniques for acquiring and storing image data, and the illustrated technique is just a non-limiting example. For convenience of illustration, FIG. 3 represents scanner 160 as directly generating image data 298.

With respect to image-analysis functions, GUI manager 310 provides user 201 with various options for analyzing an image, including how a grid is placed on an image. It is illustratively assumed that GUI manager 310 provides GUI 282A of FIG. 4 to user 201, typically in response to a user selection. User 201 employs GUI 282A to select illustrative grid aligning parameters. For example, as indicated by graphical elements 422 and 424 of a window associated with "Configuration" tab 410, user 201 may select whether grid alignment is to be done using a fixed algorithm shape with an "easy" threshold, a fixed algorithm shape with "tight" threshold, a variable algorithm shape with easy threshold, or a variable algorithm shape with tight threshold. In the illustrated implementation, a selection of "variable circle size," for instance, indicates that grid manager 330 should use circles of varying diameter independently to identify pixels to represent each probe feature in the array image.

Figure 5A:
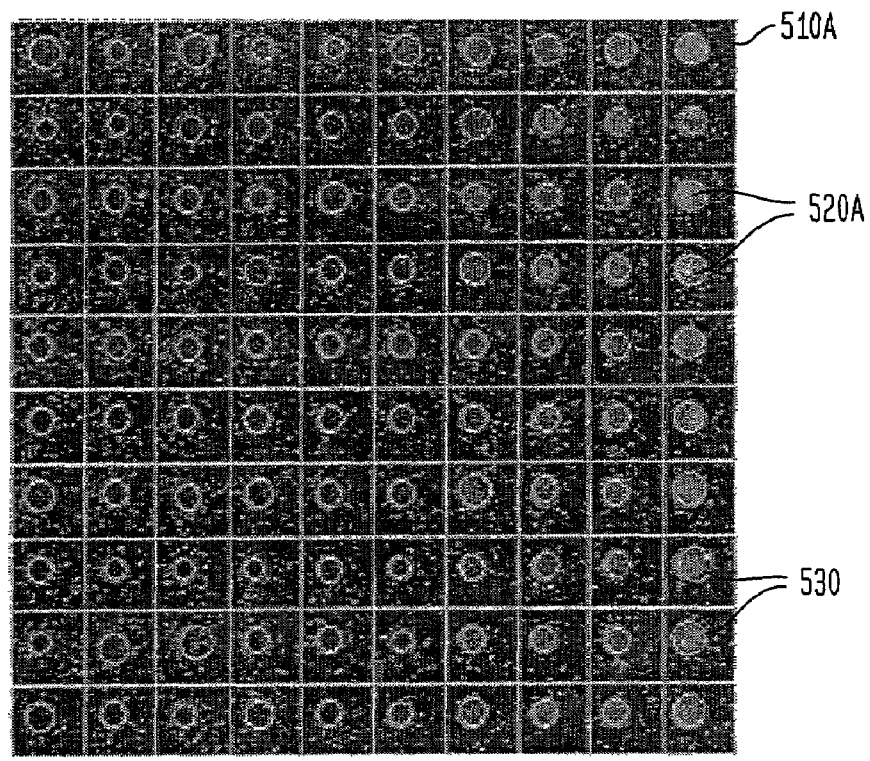
FIGS. 5A and 5B are graphical representations of scanned images showing the application of a grid and of user-specified grid parameter data.
Figure 5B:
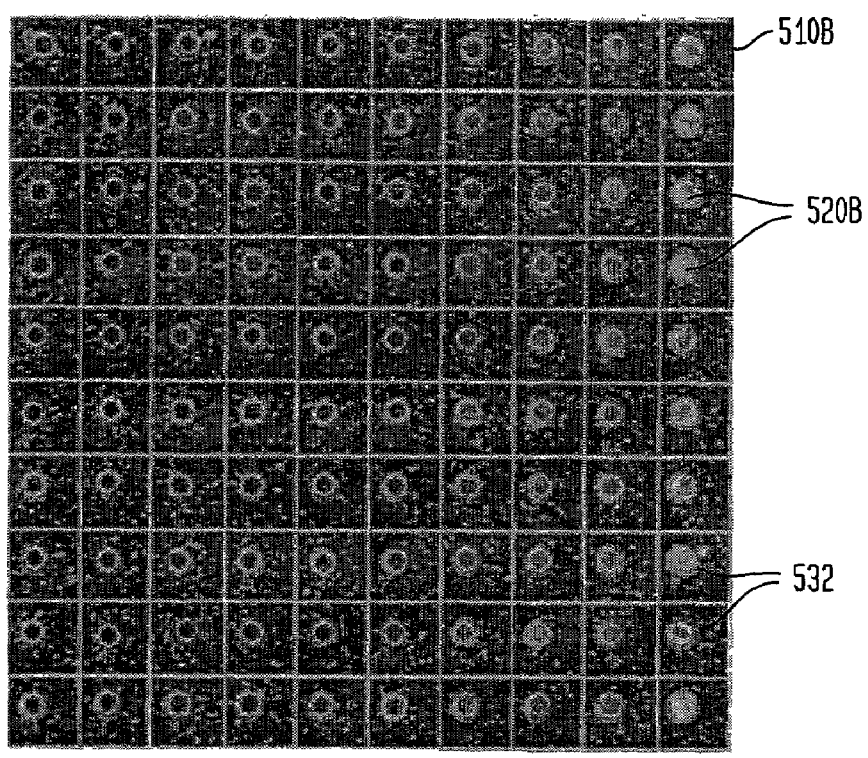

For example, FIG. 5A shows variable algorithm circles 530 such that each circle may encompass a variable number of pixels to represent the probe encircled probe feature. A "tight" threshold means that the circle should tend to be drawn around the brightest group of pixels and not include dimmer pixels that could be encompassed, for example, by a larger diameter circle. An "easy" threshold means that the dimmer pixels should tend to be included within the circle. FIG. 5B shows fixed algorithm circles 532, all of which are a same diameter, which may be user selected in some implementations. In this context, a tight threshold means that the circles tend to be centered around the brightest group of pixels, whereas an easy threshold means that dimmer pixels tend to be included in determining the center of the circle. As indicated by graphical element 420, user 201 may also select an estimated feature size. For instance, if the probe features are deposited using a pin, such as ones employed using the Pin-and-Ring™ technology of the Affymetrix® 417™ or 427™ Arrayers, then user 201 may select a pin size, e.g., 125 microns as shown in element 420.

Also included in application 290 is grid manager 330 that aligns one or more grids with one or more images of probe arrays generated by scanner 160, distinguishes between pixels representing intensities of features (e.g., hybridized probe-target pairs) and pixels representing noise or unreliable feature information, and may adjust the grid in order to better identify and locate the features. Adjusting the grid may include making local adjustments in a grid or, alternatively, imposing two or more grids over an image so that some portions of the image are divided into grid cells of a different shape and/or orientation than grid cells imposed on other portions of the same image. It is possible in this manner for each feature to have an individualized grid cell distinguishing it from neighboring features. This optional feature of imposing multiple grids over portions of an image may hereafter be referred to as "local grid alignment." One or more aspects of rid alignment data and feature intensity data generated by grid manager 330 may be stored in memory, such as represented by illustrative image analysis data file 299 in system memory 220 of computer 100. Grid alignments provided by grid manager 330 provides image analyzer 350 with feature definitions and other information to identify the pixels associated with each probe feature for purposes of analysis (such as gene expression analysis) and thus distinguish the pixels of one probe feature from the pixels of other probe features, to distinguish reliable feature pixels from unreliable ones (e.g., pixels that may reflect a scratch through a feature rather than a feature-generated intensity value), or from background pixels.

Figure 6:
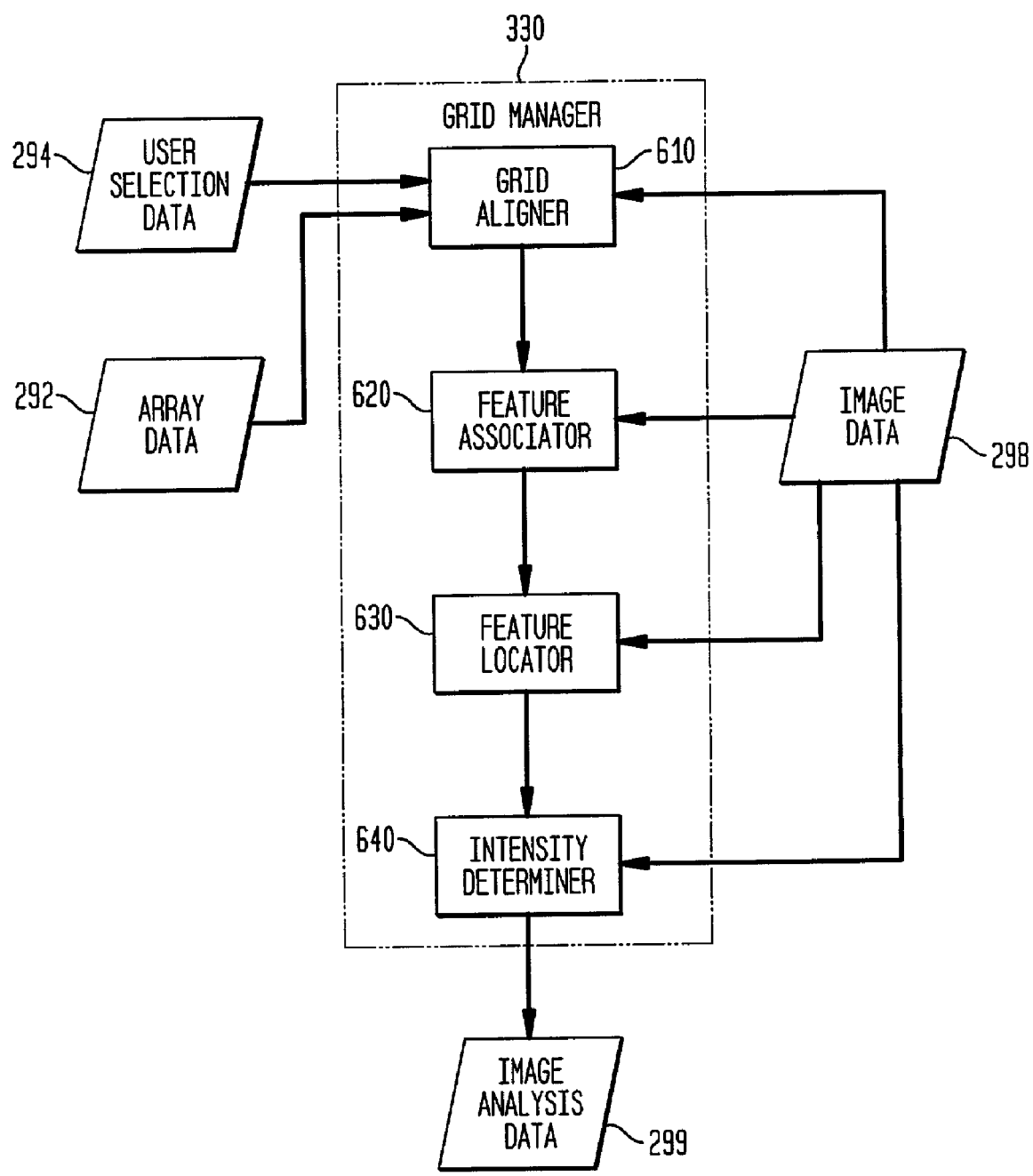
FIG. 6 is a functional block diagram of one implementation of the grid manager of the application of FIG. 3.
Figure 7:
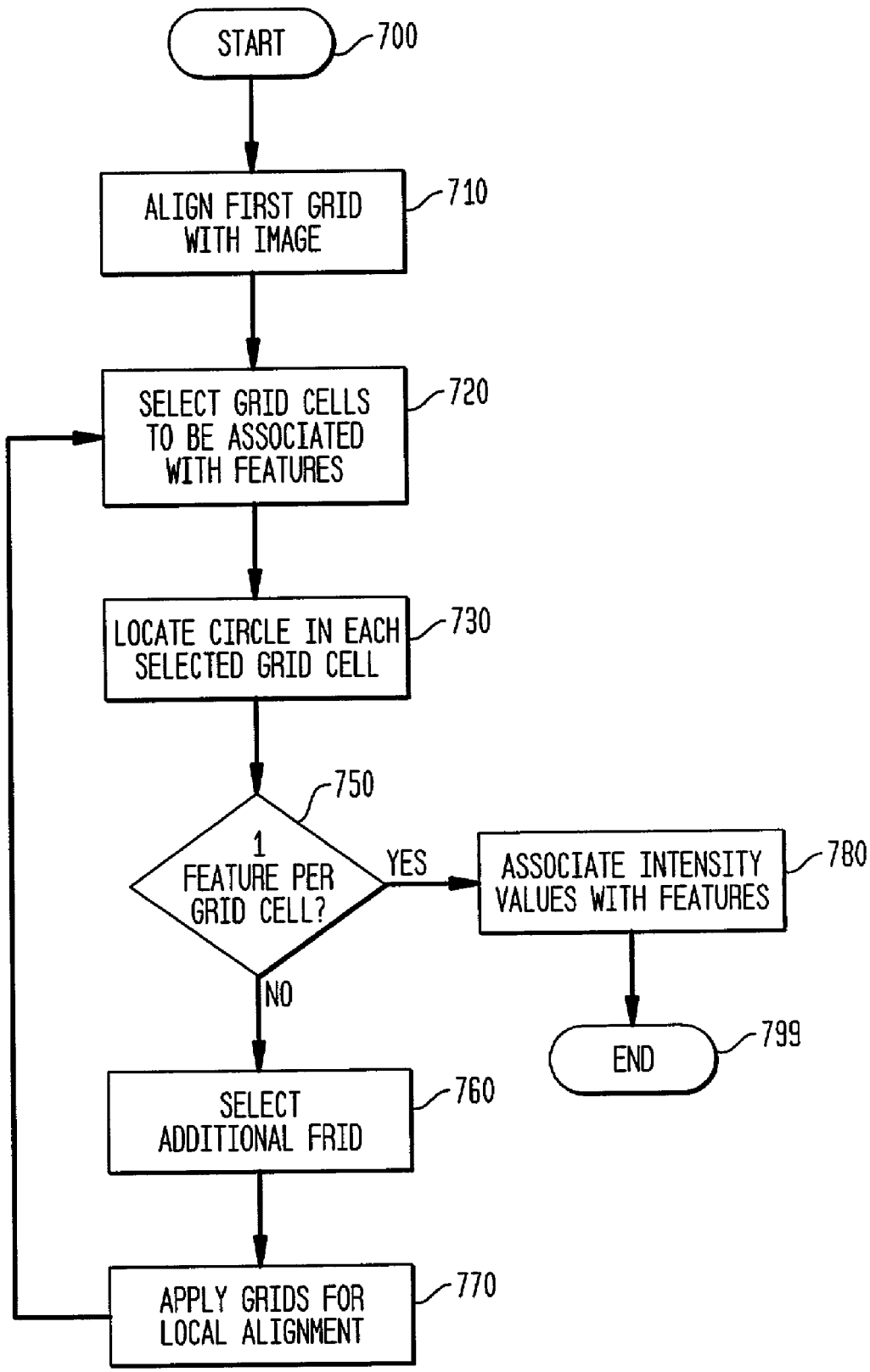
FIG. 7 is a flow diagram showing steps implemented by illustrative embodiments of the application of FIG. 3 and, in particular, the grid manager of FIG. 6.

These and other operations of manager 330 are now further described with reference to the functional block diagram of an illustrative embodiment of manager 330 as shown in FIG. 6. The relations of these operations to corresponding method steps of the illustrative flow chart of FIG. 7 are parenthetically indicated.

Grid manager 330 includes grid aligner 610 that aligns one or more grids, each having one or more grid cells, with all or portions of the image (see step 710). As noted, it often is desirable to align grids so that each grid cell circumscribes one, and only one, feature. In this implementation, when manager 330 has identified features it may occur that all or a portion of a second or additional feature is located in a same grid cell as a first feature, that features are not centrally located within grid cells, and/or that some or all features extend somewhat outside a boundary of a grid cell. These situations may occur in some portions of an image even though other portions of the same image may have perfectly aligned grid cells (e.g., all features are centrally disposed within grid cells in the aligned regions). It may be desirable in such situations to provide for local grid alignment by, for example, imposing one grid over a portion of the image and one or more other grids over other portions of the image even to the extent of having differently shaped and/or oriented grid cells associated with each feature or possible feature location (see decision element 750 and steps 760 and 770). Another element of grid manager 330 of this illustrative implementation is feature associator 620 that selects one or more grid cells to be associated with features based, at least in part, on distributions of pixel intensity values within the grid cells (see step 720). Also included in manager 330 in this implementation is feature locator 630 that selects from pixels within each selected grid cell a subset of feature pixels, or feature pixels and portions of feature pixels, based, at least in part, on distributions of pixel intensity values within the selected grid cell (see step 730 for a particular implementation). Intensity determiner 640 is yet another element in this illustrative implementation, and it is constructed and arranged to associate one or more intensity values with a feature based, at least in part, on intensities of the feature pixels, or pixels and portions of pixels, of a selected grid cell (see step 780). Each of these elements is now described separately in greater detail.

As noted, grid aligner 610 aligns one or more grids, each having one or more grid cells, with all or portions of the image. Any technique for aligning a grid with an image, now available or to be developed in the future, may be employed by aligner 610. As one non-limiting example, aligner 610 may employ any one or combination of the techniques and methods described in U.S. Pat. No. 6,090,555; U.S. patent application Ser. Nos. 09/681,819 and 09/682,076; and U.S. Provisional Patent Application Ser. No. 60/242,973, all of which have been incorporated above. Examples of alignment grids superimposed on a scanned image are shown as grid 510A of FIG. 5A and grid 510B of FIG. 5B. Although grids 510 of these figures are shown as consisting of horizontal and parallel lines, other grid configurations may be employed in other implementations. That is, the grid cells defined by the intersections of the grid lines need not be rectangles or squares, and generally may be any shape, including cells defined by curved or irregularly shaped lines. Aspects of the initial alignment of a grid with an image may be implemented using array data 292 associated with particular array types. For example, user 201 may, in the manner noted above or otherwise, have indicated that the image being analyzed corresponds to a hybridized probe array of a type having predetermined distances between probes and particular probe configurations (e.g., probes on corners of squares, on interleaved and offset rows, and so on). Probes may therefore have a predetermined relative distance between them, and/or their position may be known in absolute terms with respect to fiducial marks. As also noted, user 201 may indicate an expected size of a probe feature based, for example, on a tip diameter of a deposition pin. In other implementations, aligner 610 may analyze a region of an image to identify features (which may be fiducial features such as those "spiked" into the image using labeled agents that are known to hybridize at known locations, fluorescent markers, and so on) and determine from their configuration a general configuration for features throughout the image. For example, aligner 610 may note that fiducial or other detected features are a distance apart indicating that a probe array of a certain known type, and having a known probe configuration, has been imaged.

Feature associator 620, as noted, selects one or more grid cells to be associated with features based, at least in part, on distributions of pixel intensity values within the grid cells. In some implementations, associator 620 also identifies one or more first kernel pixels based on their location within the first-grid cell. For example, the first kernel pixels may be a single pixel at a geometric center of a grid cell, or a group of pixels around the center. Associator 620 may then determine a first measure of intensity of these first kernel pixels, for example the intensity may simply be the intensity of a single pixel at the center, or an average or other statistical measure of the intensities of pixels around the center. If this measure of intensity exceeds a first threshold, then associator 620 may select the first-grid cell as being associated with a feature, that is, it may indicate that a feature (e.g., hybridized probe-target pair) has been detected in the grid cell. The first threshold may be determined, for example, by averaging or otherwise measuring or representing the intensities of pixels near the border of the grid cell where, if the grid cell has been appropriately sized and placed, the pixels should be dim as contrasted with the bright intensities of pixels in the center where the feature is centered. If the first measure of intensity does not exceed the first threshold, associator 620 may sequentially identify one or more additional groups of kernel pixels. For instance, associator 620 may examine the intensity of a pixel adjacent to the center pixel (or a group of pixels adjacent to the center group). This group of one or more pixels may have a higher intensity than the first group due to the feature being off-center within the grid cell, the center of the feature being obscured by dust or for another reason being dim (e.g., uneven hybridization of labeled targets across the expanse of a probe spot), an irregularity in the scanner, or for another reason. Associator 620 may then determine a second measure of intensity of the sequentially identified group of kernel pixels (or it may use the same averaging or other measure previously used) and select the first-grid cell as being associated with a feature when the second measure of intensity exceeds the first threshold. This systematic searching around the territory of the grid cell may continue in accordance with any searching method until all or a pre-determined portion of the cell has been searched. If a kernel pixel has not been identified in this process, then associator 620 may indicate that the grid cell is not associated with a feature; i.e., the feature is missing. A missing feature may be due to lack of hybridization, failure of the probe to be spotted, or another cause.

User 201 may also influence this process. For example, in a particular implementation of the functions of associator 620, pixels on the four borders of a rectangular or square grid cell may be used to calculate a background intensity value for that grid cell. Associator 620 identifies the pixel at the center of the grid cell and determines whether its intensity exceeds that of a threshold based on the background intensity, subject to variation by user 201. For instance, user 201 may indicate via an appropriate one of GUI's 282 that an "easy" signal threshold should be used. Any of a variety of computations may be made, such as equating the easy signal threshold with the 75th percentile of background pixel intensities plus a value equal to 1.5 times the interquartile range (75th percentile minus 25th percentile) of the background pixels. The 75th percentile of background pixel intensities is the intensity at which 75 percent of the background pixels are dimmer, and 25 percent of the background pixels are brighter, than the adopted value. As one of numerous specific examples of a tight threshold, an estimate may be made of the half signal strength based on the background the feature pixels. For instance, associator 620 may first identify a spot feature using the easy threshold and a variable spot size, and then sort the feature pixels by intensity. The pixel intensity at the 90th percentile may be used as an estimate of the strongest signal. The tight signal threshold in this case may be calculated, for example, to be equal to the representative background intensity value plus the average of the strongest signal and that background intensity value. If the center pixel intensity exceeds the signal threshold, associator 620 may identify all pixels that are contiguous with the center pixel and that exceed the signal threshold, and these pixels may serve to define or locate the feature.

For convenience of illustration, aspects of these and other feature-definition operations are now described in further detail with respect to feature locator 630. It should be noted that the functions of associator 620 and locator 630 are separately described for convenience of illustration in respect to particular implementations, and that their functions may be combined or otherwise distributed in other implementations. In one implementation, locator 630 is constructed and arranged to identify one or more first kernel pixels based on their location within the first-grid cell (e.g., by looking first at the center of the cell and then examining pixels incrementally offset from the center, in any systematic order). When a measure of the intensity of the first kernel pixels exceeds a first threshold (as described above using grid perimeter pixels, for example) locator 630 identifies a group of additional pixels proximate to the first kernel pixels based on a measure of their intensities having a value exceeding the threshold. Locator 630 may then center a shape, such as a circle, based on the intensities and/or locations of the first kernel and additional pixels. User 201 may specify that another shape be used, such as a square or rectangle, if, for example, it is expected that the deposition or synthesis technology used to generate the probes of the probe array will generate probes of that other shape. Circles are used in the illustrated examples because depositing small amounts of liquids from pins generally results in circular spots, but non-orthogonal registration of the print head with the probe substrate may result in oval spots and many other factors may be involved in particular cases so that other shapes are anticipated. When a measure of the intensity of the first kernel pixels does not exceed the first threshold, locator 630 may identify one or more second kernel pixels based on proximity to the first kernel pixels and a measure of the intensity of the second kernel pixels exceeding the first threshold, identify a group of additional pixels proximate to the second kernel pixels based on a measure of their intensities having a value exceeding the first or a second threshold, and locate the shape based on the intensities and/or locations of the second kernel and additional pixels.

Figure 8A:
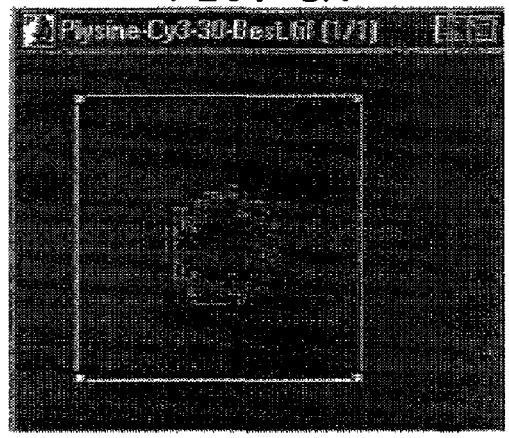
FIGS. 8A–C represent illustrative techniques by which the grid manager of FIG. 6 may locate and measure a probe feature.
Figure 8B:
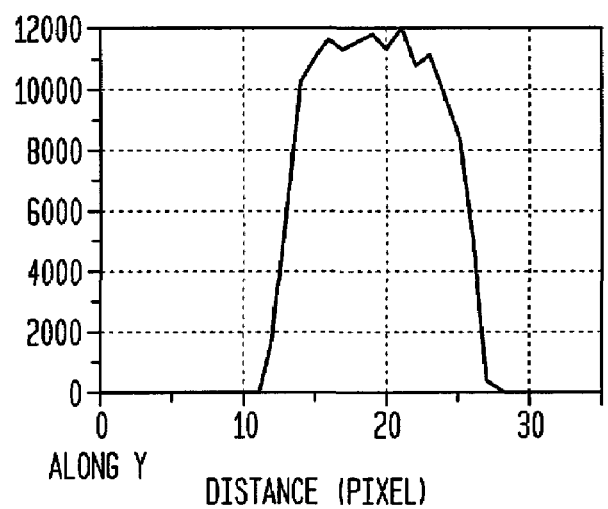
Figure 8C:
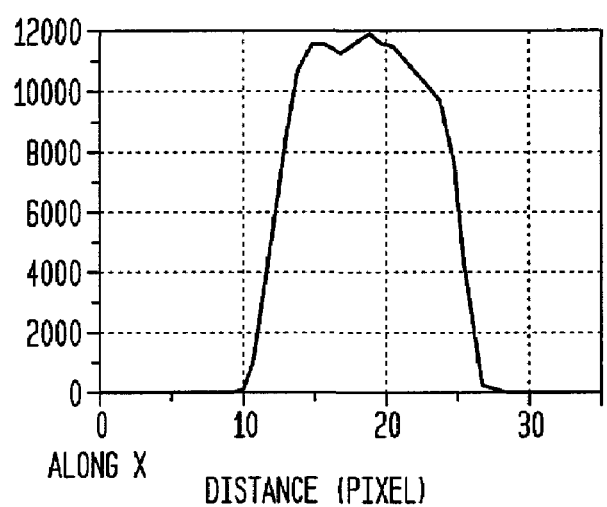

FIGS. 8A–C provide additional detail with respect to particular implementations. FIG. 8A is a graphical representation of pixels, including feature pixels and background pixels, within a single grid cell that. FIG. 8B is a plot of pixel intensities along a "y" or vertical axis, and along the orthogonal "x" axis. To locate the probe feature (brighter pixels in this case, against a background of black pixels) locator 630 finds a global signal threshold based on a histogram of pixel intensities over the entire grid image. Locator 630 then calculates the histogram of the image using 1024 bins in this example by determining the median, then calculating the quartile distance between the median and the 75th percentile (second and third quartiles). The threshold is taken as the median plus three times the quartile distance. Grids with fewer than N percent pixels of signal are designated as having no feature. Line profiles, as shown in FIGS. 8B and 8C, are taken along the x and y axes, where the profile along x is: $f(x)$=sum over y of intensity (x,y) divided by $N_y$. Similarly the profie along y is $f(y)$=sum over x of intensity (x,y) divided by $N_x$.

Figure 9A:
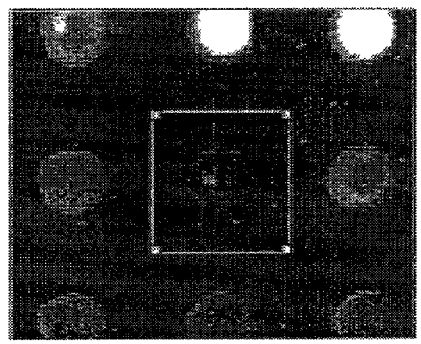
FIGS. 9A–C represent illustrative techniques by which the grid manager of FIG. 6 may distinguish contaminants from a probe feature.
Figure 9B:
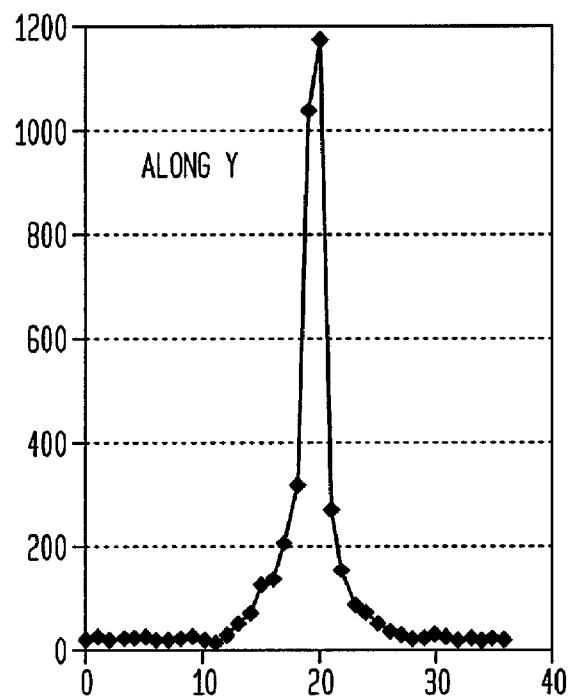
Figure 9C:
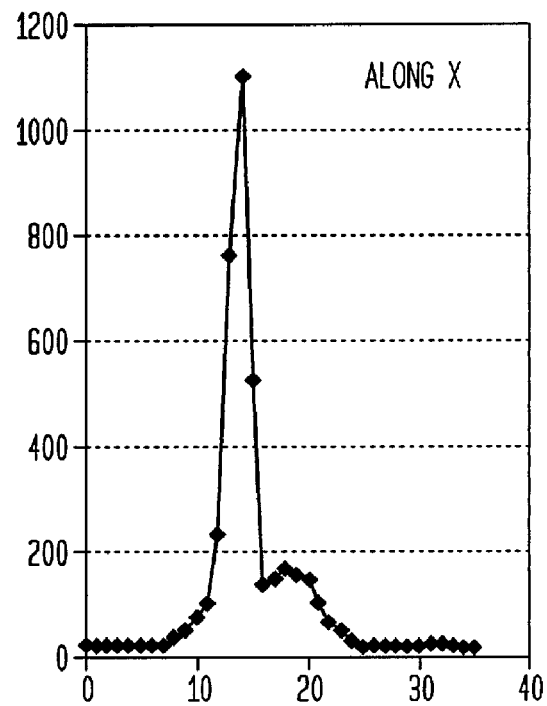

Locator 630 may also distinguish dirt or other noise signal from feature signals. FIGS. 9A–C illustrate a particular implementation. Locator 630 finds the largest peak in line profiles of a cell image, such as the image of FIG. 9A in which a dim feature includes a bright spot of dirt or other contaminant. Line profiles are taken, such as described above. If a peak is less than a predetermined or calculated amount, e.g., six pixels wide, then locator 630 assumes the signal is dirt or a non-feature signal. Contaminant detection typically is repeated until all areas of the cell have been canvassed. If there is no contaminant detected, locator 630 takes a peak width at the N percent of the maximum where, as above, N may be an empirically determined number such as 50, which may be refined based on experience. The feature diameter is calculated as the median of the profile widths across a sufficient number of profiles to cover the entire possible feature position within the cell. If contaminant is detected initially, then the calculation of the diameter of the spot may be adjusted accordingly. For example, locator 630 may ignore those points in the profile corresponding to the detected contaminant, centered about the peak. For example, the number of points to ignore may be M times the full width half maximum of the contaminant peak. M may be empirically chosen, such as 2 for an initial estimate, and adjusted based on experience. The x and y positions of the feature are calculated, in a particular implementation, as the mid points of the line profiles between the half maximum values.

Figure 10A:
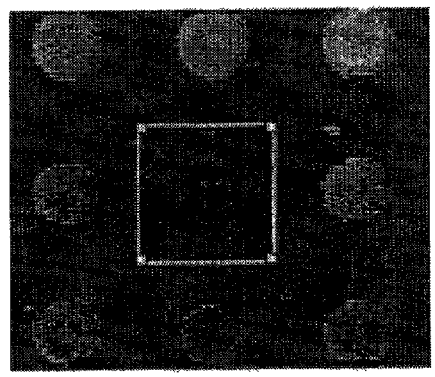
FIGS. 10A–C represent illustrative techniques by which the grid manager of FIG. 6 may identify an unusually shaped probe feature.
Figure 10B:
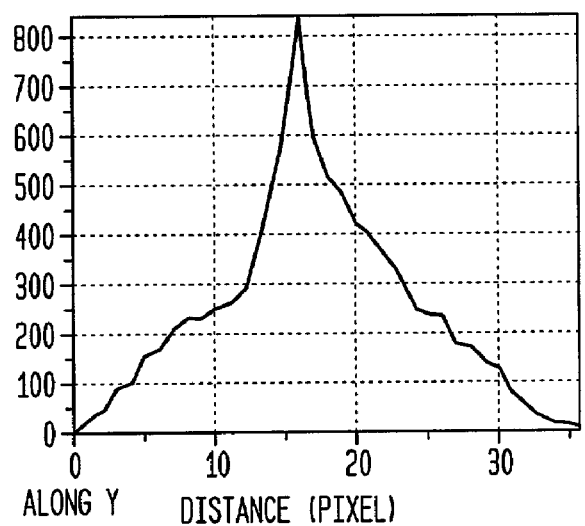
Figure 10C:
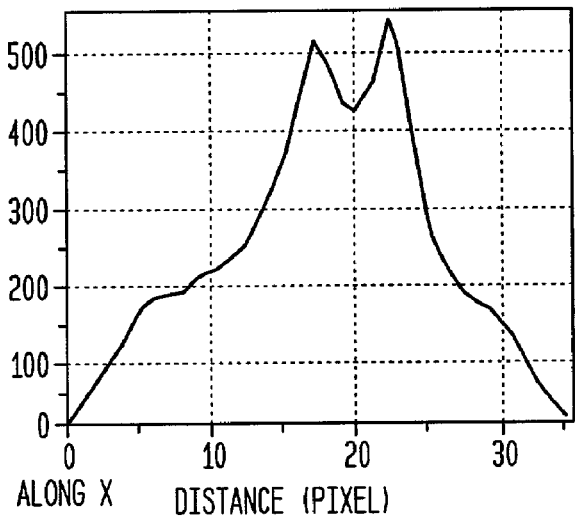

Locator 630 may also detect unusually shaped features based, for example, on their having an unexpected intensity profile across one or more dimensions. For example, FIG. 10A shows an unusually shaped spot within a single grid cell. Features of unusual shape typically have a profile that is unusual compared to those of regularly shaped features, based on empirical examination or calculations of anticipated shapes. For example, the ratio of full width half maximum to the ratio of full width at a tenth of maximum may appear for some unusually shaped features, such as the one shown, to be much larger than that of regularly shaped spots. Line profiles showing this basis for discrimination are shown in FIGS. 10B and 10C.

As noted, intensity determiner 640 is constructed and arranged in the illustrated implementation to associate one or more intensity values with a feature based, at least in part, on intensities of the feature pixels, or pixels and portions of pixels, of a selected grid cell. For example, an initial estimate of feature intensity may be the median intensity of the pixels within the circle (or other shape in other implementations) located within the grid cell and around the feature. Another approach is to identify feature pixels by performing a histogram analysis within the grid cell. For example, the histogram bin size may be set to be the median divided by N, where an initial estimate of N may be 8 or another empirically determined or calculated number. If it generally expected that the histogram will have two modes, background and signal. If contamination is present, there may be a third mode. Pixels are ignored if they fall in the smaller area of the histogram. Pixels are also ignored if they are based on small peaks in line profiles. Further, pixels that are too dim or too bright, i.e., at the extremes of the histogram, may be ignored. The shape of the profiles may indicate the spot quality. Additional spot quality values may be determined in accordance with numerous statistical approaches. For example, a perimeter may be calculated using a likelihood matrix, and a comparison made of the perimeter-via-likelihood versus the perimeter-via-pixel count. The perimeter-via-pixel count in one implementation equals the square root of the area (pixel count of pixels belonging to the feature) divided by two pi. Background pixels may be found by many techniques, such as by ignoring the area in profile peaks. First a histogram of pixels is taken. Then pixels brighter than (or dimmer than) a selected percentile, e.g., eightieth percentile, are ignored.

Having described various embodiments and implementations of the present invention, it should be apparent to those skilled in the relevant art that the foregoing is illustrative only and not limiting, having been presented by way of example only. Many other schemes for distributing functions among the various functional elements of the illustrated embodiment are possible in accordance with the present invention. The functions of any element may be carried out in various ways in alternative embodiments. Also, the functions of several elements may, in alternative embodiments, be carried out by fewer, or a single, element.

Similarly, operations of a particular functional element that are described separately for convenience need not be carried out separately. For example, the functions of application manager 305, GUI manager 310, image analyzer 350, and grid aligner 330 as described above could be performed by any one or more of them, and/or by another element, in other implementations. The functions described with respect to manager 305, manager 310, analyzer 350, and aligner 330 are separated into distinct functional elements simply for convenience and clarity of illustration. Similarly, the functions of elements 610, 620, 630, and 640 are separated in the figures and separately described for convenience of illustration, and may be otherwise arranged, combined, or distributed in other embodiments. In the same vein, in some embodiments any functional element may perform fewer, or different, operations than those described with respect to the illustrated embodiment. Also, functional elements shown as distinct for purposes of illustration may be incorporated within other functional elements in a particular implementation.

Furthermore, the sequencing of functions or portions of functions generally may be altered. For example, the method steps shown in FIG. 7 generally need not be carried out in the order suggested by this figure. Among many possible examples, steps 720 and 730 could be combined or carried out in parallel, steps 720 or 730 could be carried out after step 780 or after decision element 750, and so on.

In addition, it will be understood by those skilled in the relevant art that control and data flows between and among functional elements of the invention and various data structures may vary in many ways from the control and data flows described above. More particularly, intermediary functional elements (not shown) may direct control or data flows, and the functions of various elements may be combined, divided, or otherwise rearranged to allow parallel and/or distributed processing or for other reasons. Also, intermediate data structures or files may be used, various described data structures or files may be combined, the sequencing of functions or portions of functions generally may be altered, and so on. It further will be understood that references herein to such terms as "file," "data structure," or "database" are illustrative only and that, in various implementations, data stored in a file may alternatively be stored in a database or otherwise stored in accordance with techniques and conventions familiar to those of ordinary skill in the relevant art. Data stored in files, databases, or other structures or in accordance with other techniques may be stored locally and/or may be stored remotely, e.g., data may be distributed over a number of local and/or remote files or databases. Databases may be flat, relational, object oriented, or structured in accordance with other techniques known to those of ordinary skill in the relevant art or that may be developed in the future. Numerous other embodiments, and modifications thereof, are contemplated as falling within the scope of the present invention as defined by appended claims and equivalents thereto.

What is claimed is:

1. A method for analyzing biological activity from a pixilated scanned image of a probe array, wherein the image includes a plurality of features corresponding to emissions detected from the probe array, comprising the steps of:
   (a) aligning a first grid having one or more first-grid cells with a first portion of the image;
   (b) selecting one or more cells of the aligned first-grid cells each selected cell associated with one of the features, wherein each cell is selected when a distribution of a first set of one or more pixels each comprising an intensity value are located at or near a center position of an area bounded by a plurality of grid lines defining the cell and an average of the intensity values of the first set of pixels exceeds a threshold value;
   (c) selecting a second set of one or more pixels proximate to the pixels of the first set within each selected cell, wherein each pixel of the second set comprises an intensity value that exceeds the threshold;
   (d) associating an intensity value with the feature of each selected cell, wherein the intensity value associated with the feature is an average value of the intensities of the pixels in the first and second sets;
   (e) aligning a second grid having one or more second-aid cells with a second portion of the image;
   (f) selecting one or more cells of the aligned second-grid cells each selected cell associated with one of the features, wherein each cell is selected when a distribution of a first set of one or more pixels each comprising an intensity value are located at or near a center position of an area bounded by a plurality of grid lines defining the cell and an average of the intensity values of the first set of pixels exceeds a threshold value;
   (g) selecting a second set of one or more pixels proximate to the pixels of the first set within each selected cell, wherein each pixel of the second set comprises an intensity value that exceeds the threshold value; and
   (h) associating an intensity value with the feature of each selected cell, wherein the intensity value associated with the feature is an average value of the intensities of the pixels in the first and second sets.

2. The method of claim 1, wherein:
the probe array is a spotted probe array and the features correspond to spots of biological material including any one or more of nucleic acid, peptide, protein fragment, protein, antibody, ligand, receptor, or small molecule.

3. The method of claim 1, wherein:
the first-grid cells and second-grid cells have a rectangular or square shape.

4. The method of claim 1, wherein:
one or more the first-grid cells are of a different size or orientation than one or more of the second-grid cells.

5. The method of claim 1, wherein:
the step of aligning the first grid includes determining that each first-grid cell circumscribes no more than one complete feature.

6. A method for analyzing a pixilated image having a plurality of features corresponding to emissions detected from a probe array, comprising the steps of:
   (a) aligning a first grid having one or more first-grid cells with a first portion of the image;
   (b) selecting one or more cells of the aligned first-grid cells each selected cell associated with one of the features, wherein each cell is selected when a distribution of a first set of one or more pixels each comprising an intensity value are located at or near a center position of an area bounded by a plurality of grid lines defining the cell and an average of the intensity values of the first set of pixels exceeds a threshold value;
   (c) locating a shape comprising an anticipated dimension of the feature of each selected cell, wherein the positional location of the shape is determined using the position of the first set of pixels and a second set of one or more pixels proximate to the pixels of the first set, wherein each pixel of the second set comprises an intensity value that exceeds the threshold value;
   (d) associating an intensity value with the feature of each selected cell, wherein the intensity value associated with the feature is an average value of the intensities of the pixels;
   (e) aligning a second grid having one or more second-grid cells with a second portion of the image;
   (f) selecting one or more cells of the aligned second-grid cells each selected cell associated with one of the features, wherein each cell is selected when a distribution of a first set of one or more pixels each comprising an intensity value are located at or near a center position of an area bounded by a plurality of grid lines defining the cell and an average of the intensity values of the first set of pixels exceeds a threshold value;
   (g) locating a second shape comprising an anticipated dimension of the feature of in each selected cell, wherein the positional location of the shape is determined using the position of the first set of pixels and a second set of one or more pixels proximate to the pixels of the first set, wherein each pixel of the second set comprises an intensity value that exceeds the threshold value; and (h) associating an intensity value with the feature of each selected cell, wherein the intensity value associated with the feature is an average value of the intensities of the pixels located within the shape.

7. The method of claim 6, wherein:
the probe airay is a spotted probe array and the features correspond to spots of biological material.

8. The method of claim 7, wherein:
the biological material includes any one or more of nucleic acid, peptide, protein fragment, protein, antibody, liganct receptor, or small molecule.

9. The method of claim 8, wherein:
the biological material is deposited in pre-synthesized or pre-selected form onto the spots.

10. The method of claim 9, wherein:
the biological material is synthesized in situ.

11. The method of claim 6, wherein:
the emissions include fluorescent emissions.

12. The method of claim 6, wherein:
the step of aligning the first grid employs expected locations of probes of the probe array.

13. The method of claim 12, wherein:
the expected locations are predetermined by relative or absolute locations of probes on a probe-array type having a predetermined configuration of probes, wherein the probe-array type is correlated with the probe array.

14. The method of claim 12, wherein:
the expected locations are defined by user-specified information.

15. The method of claim 6, wherein:
the first-grid cells each have shape and dimensions defined by a predetermined configuration of probes on a probe-array type correlated with the probe array.

16. The method of claim 15, wherein:
the probe-array type is correlated with the probe using one or more user selections.

17. The method of claim 15, wherein:
the probe-array type is correlated with the probe array via detection of two or more features.

18. The method of claim 6, wherein:
the first portion is all of the image.

19. The method of claim 6, wherein:
the first portion is less than all of the image and is determined using a user selection of a region of interest of the image.

20. The method of claim 6, wherein:
the first portion is less than all of the image and is determined using a measure of fitness of features within the first-grid cells.

21. The method of claim 6, wherein:
the first and/or second shapes are circles.

22. The method of claim 21, wherein:
the circles have a user-selected diameter.

23. The method of claim 21, wherein:
the user-selected diameter corresponds to a characteristic of a spot depositing element.

24. The method of claim 6, wherein:
the probe array includes two subarrays, the first grid is aligned with a first of the subarrays, and the second grid is aligned with a second of the subarrays.

25. The method of claim 6, wherein:
the threshold value comprises a value derived from intensity values associated with one or more pixels proximate to one or more borders of each selected cell.

26. A computer program product for analyzing a pixilated image of a probe array stored for execution in system memory of a computer, wherein the image includes a plurality of features corresponding to emissions detected from the probe array, comprising;
a grid aligner that aligns a first grid with a first portion of the image and a second grid with a second portion of the image, each grid having one or more grid cells;
a feature associator that selects one or more cells from each of the aligned first and second grid cells each selected cell associated with one or more of the features, wherein each cell is selected when a distribution of a first set of one or more pixels each comprising an intensity value are located at or near a center position of an area bounded by a plurality of grid lines defining the cell and an average value of the intensity values of the first set of pixels exceeds a threshold value; and
a feature locator that selects a second set of one or more pixels proximate to the pixels of the first set within each selected cell, wherein each pixel of the second set comprises an intensity value that exceeds the threshold value.

27. The product of claim 26, further comprising:
an intensity determiner that associates an intensity value with the feature of each selected cell, wherein the intensity value associated with the feature is an average value of the intensities of the pixels in the first and second sets.

28. A computer program product stored for execution in system memory of a computer for analyzing a pixilated image having a plurality of features corresponding to emissions detected from a probe array, comprising:
a grid that aligns a first grid with a first portion of the image and a second grid with a second portion of the image, each grid having one or more grid cells;
a feature associator that selects one or more cells from each of the aligned first and second grid cells each selected cell associated with one of the features, wherein each cell is selected when a distribution of a first set of one or more pixels each comprising an intensity value are located at or near a center position of an area bounded by a plurality of grid lines defining the cell and an average of the intensity values of the first set of pixels exceeds a threshold value;
a feature locator that locates a shape comprising an anticipated dimension of the feature of each selected cell, wherein the positional location of the shape is determined using the position of the first set of pixels and a second set of one or more pixels proximate to the pixels of the fast set, wherein each pixel of the second set comprises an intensity value that exceeds the threshold value; and
an intensity determiner that associates an intensity value with the feature of each selected cell, wherein the intensity value associated with the feature is an average value of the intensities of the pixels located within the shape.

29. The product of claim 28, wherein:
the probe array is a spotted probe array and the features correspond to spots of biological material including any one or more of nucleic acid, peptide, protein fragment, protein, antibody, ligand, receptor, or small molecule.

30. The product of claim 28, wherein:
the shape is a circle.

31. The product of claim 28, wherein:
the threshold value comprises a value derived from intensity values associated with one or more pixels proximate to one or more borders of each selected cell.

32. A scanning system, comprising:
a scanner that scans a probe array to generate a pixilated image having a plurality of features corresponding to emissions detected from the probe array;
a computer having a processor and memory unit; and
a computer program product stored for execution by the processor in the memory unit, comprising a grid aligner that aligns a first grid with a first portion of the image and a second grid with a second portion of the image each grid having one or more grid cells, a feature associator that selects one or more cells from each of the aligned first and second grid cells each selected cell associated with one or more of the features, wherein each cell is selected when a distribution of a first set of one or more pixels each comprising an intensity value are located at or near a center position of an area bounded by a plurality of grid lines defining the cell and an average of the intensity values of the first set of pixels exceeds a threshold value, a feature locator that locates a shape comprising an anticipated dimension of the feature of each selected cell, wherein the positional location of the shape is determined using the position of the first set of pixels and a second set of one or more pixels proximate to the pixels of the first set, wherein each pixel of the second set comprises an intensity value that exceeds the threshold value, and an intensity determiner that associates an intensity value with the feature of each selected cell, wherein the intensity value associated with the feature is an average value of the intensities of the pixels located within the shape.

* * * * *